United States Patent [19]

Maulding et al.

[11] Patent Number: 4,814,486

[45] Date of Patent: Mar. 21, 1989

[54] METHOD FOR THE PREPARATION OF ANILINOFUMARATE

[75] Inventors: Donald R. Maulding, Somerville; Albert A. Cevasco, Belle Meade, both of N.J.

[73] Assignee: American Cyanamid Company, Stamford, Conn.

[21] Appl. No.: 101,453

[22] Filed: Oct. 1, 1987

[51] Int. Cl.[4] ............................................ C07C 101/44
[52] U.S. Cl. ...................................... 560/44; 546/170
[58] Field of Search ...:....................... 560/44; 546/170

[56] References Cited

U.S. PATENT DOCUMENTS

| | | | |
|---|---|---|---|
| 4,459,409 | 6/1984 | Ladner | 546/170 |
| 4,518,780 | 5/1985 | Barton et al. | 546/183 |
| 4,638,068 | 1/1987 | Los | 546/170 |
| 4,656,283 | 4/1987 | Doehner | 560/44 |
| 4,675,432 | 6/1987 | Maulding | 560/44 |

Primary Examiner—Bruce D. Gray
Attorney, Agent, or Firm—Estelle J. Tsevdos

[57] ABSTRACT

The present invention relates to an improved method for the preparation of anilinofumarates useful as intermediates in the preparation of 2-(2-imidazolin-2-yl) quinoline-3-carboxylic acid herbicidal agents.

3 Claims, No Drawings

METHOD FOR THE PREPARATION OF ANILINOFUMARATE

BACKGROUND OF THE INVENTION

The present invention relates to novel methods for preparing anilinofumarates in order to prepare quinoline-2,3-dicarboxylic acids. These acids are useful intermediates in the preparation of herbicidal pyridine and quinoline imidazolinone herbicidal compounds.

The herbidical pyridine and quinoline imidazolinone compounds prepared from the present compounds include 2-(4-isopropyl-4-methyl-5-oxo-2-imidazolin-2-yl)quinoline-3-carboxylic acid, and esters and salts thereof and are disclosed in U.S. Pat. No. 4,638,068, incorporated herein by reference. These herbicidal imidazolinyl quinolinecarboxylic acids may be prepared by the procedure described in U.S. Pat. No. 4,518,780 (incorporated herein by reference) by cyclization, under basic conditions, with an appropriately substituted 2-carbamoyl quinoline-3-carboxylic acid, that, in turn, is prepared by the reaction of a substituted quinoline-2,3-dicarboxylic acid anhydride and appropriately substituted aminocarboxamide or aminothiocarboxamide. Quinoline-2,3-dicarboxylic acid anhydrides are readily prepared from the diacids by procedures well known in the art. However, the diacids themselves are not readily available.

U.S. Pat. No. 4,656,283 describes a method useful for the preparation of quinoline-2,3-dicarboxylic acid and esters thereof by reacting a beta-anilino-alpha,beta-unsaturated ester with an immonium salt (commonly called a Vilsmeier reagent). The beta-alpha,beta-unsaturated esters are obtained by the reaction of appropriately substituted anilines with keto-esters or dialkyl acetylene dicarboxylates. This overall reaction for the preparation of quinoline-2,3-dicarboxylates is illustrated in Flow Diagram I.

FLOW DIAGRAM I

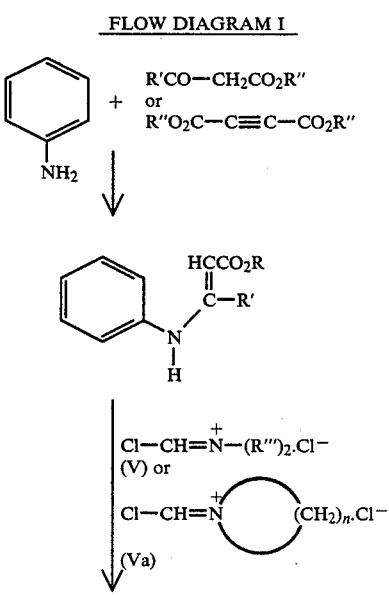

-continued
FLOW DIAGRAM I

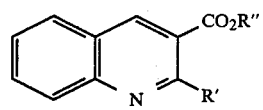

n = 4 or 5 wherein R' is $CH_3$ or $CO_2R''$ and R'' is $C_1$-$C_4$ alkyl, and R'''' is $CH_3$ or $C_1$-$C_4$ alkyl.

When R'' is $CH_3$, the diacid is obtained by concurrent oxidation and hydrolysis of the product under aqueous basic conditions in the presence of nickel peroxide, as decribed in U.S. Pat. No. 4,459,409 (incorporated herein by reference).

Unfortunately, the availability of ketoesters and dialkyl acetylene dicarboxylates, such as diethyloxalacetate and diethyl acetylenedicarboxylate, is limited, thus restricting the quantities of anilinofumarate and quinoline-2,3-dicarboxylic acid, the intermediates required for preparing herbicidal 2-(4-isopropyl-4-methyl-5-oxo-2-imidazolin-2-yl)quinoline-3-carboxylic acid, ester and salts thereof.

Pending application for U.S. patent of D. Maulding, Ser. No. 902,275, filed Aug. 29, 1986 describes a method for the preparation of anilinofumarates by the reaction of dichlorosuccinates with specific amines and the subsequent displacement of the amine with aniline in the presence of an organic acid.

U.S. Pat. No. 4,675,432 describes a method for the preparation of anilinofumarates in which dichlorosuccinates are reacted with aniline in an organic solvent in the presence of aqueous base and a phase transfer catalyst in a temperature in the range of 20° C. to 90° C. for one to 24 hours.

SUMMARY OF THE INVENTION

The present invention overcomes not only the limitations of providing a readily-available source of quinoline-2,3-dicarboxylic acid, esters and salts thereof but also provides an improvement in the reaction of dichlorosuccinates with aniline resulting in significantly increased productivity and reduction in reaction times.

Therefore, it is an object of the present invention to provide an improved method for the preparation of anilinofumarates utilizing dichlorosuccinates, obtainable from readily available dialkyl maleates, and hence, an improved method for the manufacture of large quantities of quinoline-2,3-dicarboxylic acid and esters thereof and subsequent production of herbicidal 2-(4-isopropyl-4methyl-5-oxo-2-imidazolin-2-yl)-quionoline-3-carboxylic acid, esters and salts. This and other objects of the invention will become apparent by the following description of the invention.

DETAILED DESCRIPTION OF THE INVENTION

The present invention relates to an improved method for preparing anilinofumarates and quinoline-2,3-dicarboxylic acids and esters thereof. The method comprises reacting a dichlorosuccinate (formula I)

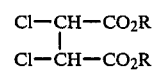

with a molar equivalents of aniline and a minimum of two molar equivalent of aqueous base in the presence of a tri- or tetra-alkylammonium phase transfer catalyst at a temperature in a range of about 85° C. to 100° C. for about one to four hours in the absence of a solvent, and isolating the thus-formed anilinofumarate.

Quinoline-2,3-dicarboxylate acid is then prepared from the thus-formed anilinofumarate by reacting the anilinofumarate with an approximately equimolar amount of a Vilsmeier reagent (immonium salt) in the presence of a hydrocarbon solvent such as toluene or a chlorinated hydrocarbon solvent such as methylene chloride, dichloroethane, ortho dischlorobenzene, chlorobenzene, or mixtures thereof, at a temperature of about 40° C. and 130° C., for a period of time sufficient to essentially complete the reaction and yield a dialkyl quinoline-2,3-dicarboxylate. This quinoline-2,3-dicarboxylate is hydrolyzed, under either acid or basic conditions, to give quinoline-2,3-carboxylic acid. This procedure is described in U.S. Pat. No. 4,656,283.

The above reactions are graphically illustrated in Flow Diagrams IIA-B.

FLOW DIAGRAM IIA

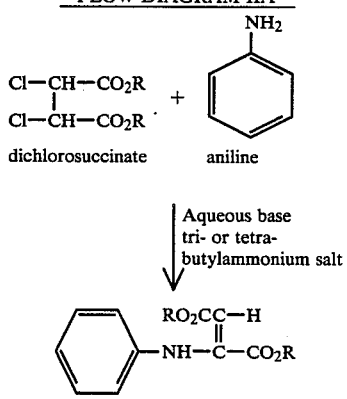

dichlorosuccinate     aniline

| Aqueous base
| tri- or tetra-
| butylammonium salt

FLOW DIAGRAM IIB

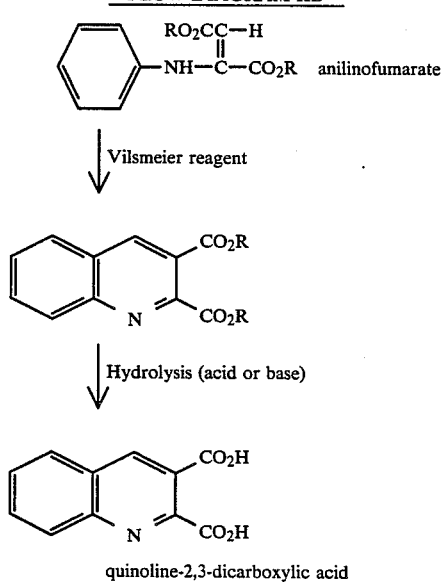

wherein R is described in formula I.

Surprisingly, it has been found that the reaction of aniline with dialkyldichlorosuccinates by the method of this invention without a solvent and preferably in the presence of a tri- or tetra-butyl-ammonium salt phase transfer catalyst results in reduced reaction times and improved productivity of the production of anilinofumarate.

The novel method of the present invention thus provides a simple and more efficient method for the production of anilinofumarate. This method, in turn, reduces handling, processing, effluent and solvents, resulting in a process that is cleaner, safer, cheaper and more efficient than prior reported methods.

In accordance with the method of this invention, diethyl dichlorosuccinate (0.053 mol), which may be prepared by the method described in Japanese Pat. No. 71 21, 564, is reacted with aniline (0.053 mol) by stirring the mixture in the presence of 0.08 molar equivalents of aqueous sodium carbonate (20% $Na_2CO_3$ w/w) and a catalytic amount (5 mol %) of tetrabutylammonium bromide at 95° C. for two hours and 30 minutes. The thus-formed anilinofumarate is readily isolated by separating off the organic phase from the aqueous slat phase.

Aqueous bases suitable for the preparation of anilinofumarate by the present method include sodium and potassium hydroxide, carbonate and bicarbonate at concentrations of 15% to 50%, by weight, in amounts sufficient to provide about two molar equivalents. The carbonates being employed in from one to three molar equivalents and the hydroxides and bicarbonates being employed in from two to three molar equivalents.

The quaternary ammonium phase transfer catalysts N-methyl-tri-n-butylammonium or tetra-n-butylammonium chloride, bromide and bisulfate, in amounts as little as 0.025 molar equivalent, have demonstrated comparable results and are preferred for the method of this invention.

The method of the present invention is further illustrated by the following examples, which are illustrative and not limitative thereof.

EXAMPLE 1

Preparation of dichlorosuccinate

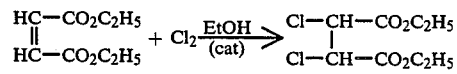

Chlorine gas is bubbled into an ethylene dichloride solution of diethyl maleate containing ethanol, (0.1 molar equivalents). After stirring the mixture at room temperature for eight hours, it is flushed with nitrogen gas for five minutes and the solvent removed under reduced pressure to yield the dichlorosuccinate in 94% yield.

EXAMPLE 2

Improvement obtained in the preparation of diethyl anilinofumarate utilizing the method of this invention

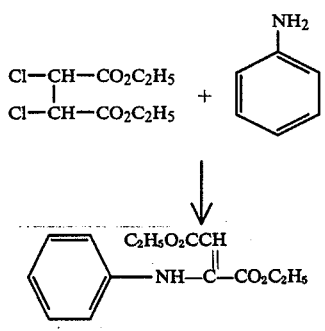

reagent or 66.5% yield based on the real diethyl dichlorosuccinate charged.

Utilizing the above procedure, aniline is reacted with diethyl dichlorosuccinate in the presence of sodium carbonate with various phase transfer catalysts, in both the presence or absence of an organic solvent at about 80° C. to 95° C. The product is isolated and analyzed by gas chromatography (GC) in order to demonstrate the improvement obtained by the method of the present invention over prior methods. The results of these experiments which are summarized in Table I below demonstrate the improvement obtained by utilizing the method of this invention.

TABLE I

| | Molar ratio diethylchloro-succinate/aniline | Phase transfer catalyst/mol % | Molar Base/equivalents | Solvents | Temp. °C. | Time to completion hrs | Product anilinofumarate GC area % |
|---|---|---|---|---|---|---|---|
| Comparative Examples | 1/1 | tricaprylmethyl-ammonium chloride/5 | Na$_2$CO$_3$ 20%/1.25 | Toluene | 80–82 | 10 | 83.0 |
| | 1/1.05 | tricaprylmethyl-ammonium chloride/5 | Na$_2$CO$_3$ 20%/1.5 | None | 80 | 8 | 68.8 |
| | 1/1 | tetra-n-butyl-ammonium bromide/5 | Na$_2$CO$_3$ 20%/1.51 | Toluene | 80 | 10 | 86.4 |
| | 1/1 | tricaprylmethyl-ammonium chloride/5 | Na$_2$CO$_3$ 20%/1.5 | None | 95 | 2 | 71.1 |
| | 1/1 | benzyltriethyl-ammonium chloride | Na$_2$CO$_3$ 20%/1.5 | None | 95 | 3 | 71.5 |
| Method of the Invention | 1/1 | tetra-n-butyl-ammonium bromide/5 | Na$_2$CO$_3$ 20%/1.51 | None | 95 | 2.5 | 92.7 |
| | 1/1 | tetra-n-butyl-ammonium bisulfate/5.7 | Na$_2$CO$_3$ 20%/1.51 | None | 95 | 1.5 | 90.4 |
| | 1/1 | tetra-n-butyl-ammonium chloride/5.7 | Na$_2$CO$_3$ 20%/1.51 | None | 95 | 1.5 | 91.2 |
| | 1/1 | N—methyl-tri-n-butyl-ammonium chloride/5.7 | Na$_2$CO$_3$ 20%/1.51 | None | 95 | 2.3 | 88.5 |

Tetra-n-butylammonium bromide (0.9 g, 0.002% mol) is added to a 25% aqueous solution of sodium carbonate (8.5 g, 0.08 mol). Diethyl dichlorosuccinate (12.9 g real, 0.053 mol) is added at 20° C.–25° C. followed by aniline (4.5 g, 0.0483 mol). The reaction mixture is heated to 95° C. over 30 minutes and held at this temperature for 1.7 hours. The phases are separated at 50° C.–75° C. A portion of the solvent required for the next step can be added to increase the rate of this phase separation.

The organic product phase is cooled to 25° C. and washed with 8–10 g of 5% hydrochloric acid to remove excess aniline. The anilinofumarate product layer is dried by azeotropic distillation.

The crude yield (14.7 g) assays as 63.1% anilinofumarate. This is a 73% yield based on aniline as the limiting

What is claimed is:

1. An improved method for the preparation of anilinofumarate wherein dichlorosuccinate of formula

wherein R is C$_1$–C$_4$ alkyl is reacted with a molar equivalent of aniline in the presence of 2 or greater molar equivalents of an aqueous base, said improvement comprising: conducting the above reaction in the presence of a tri- or tetraalkylammonium salt phase transfer catalyst at a temperature of about 85° C. to 100° C. for one to four hours in the absence of an organic solvent.

2. A method according to claim 1, wherein said aqueous base is 15% to 50%, on a weight basis, of sodium hydroxide, carbonate or bicarbonate or potassium hydroxide, carbonate or bicarbonate, or mixtures thereof.

3. A method according to claim 2, wherein said phase transfer catalyst is tetra-n-butyl-ammonium bromide, chloride or bisulfate or N-methyl-tri-n-butyl-ammonium bromide, chloride or bisulfate.

* * * * *